US007622156B2

(12) United States Patent
Watling

(10) Patent No.: US 7,622,156 B2
(45) Date of Patent: Nov. 24, 2009

(54) COLOURING MASONRY SURFACES

(75) Inventor: Anthony John Watling, St. Ives (AU)

(73) Assignee: Nawkaw Holdings B.V., Amsterdam (NL)

( * ) Notice: Subject to any disclaimer, the term of this patent is extended or adjusted under 35 U.S.C. 154(b) by 342 days.

(21) Appl. No.: 10/534,230

(22) PCT Filed: Nov. 6, 2003

(86) PCT No.: PCT/AU03/01472

§ 371 (c)(1),
(2), (4) Date: May 6, 2005

(87) PCT Pub. No.: WO2004/041749

PCT Pub. Date: May 21, 2004

(65) Prior Publication Data

US 2006/0157895 A1 Jul. 20, 2006

(30) Foreign Application Priority Data

Nov. 7, 2002 (AU) .............................. 2002301894

(51) Int. Cl.
*B05D 1/00* (2006.01)

(52) U.S. Cl. ....................................... 427/403; 427/140

(58) Field of Classification Search ................. 264/294, 264/638; 249/16; 427/140, 403
See application file for complete search history.

(56) References Cited

U.S. PATENT DOCUMENTS

| | | | | |
|---|---|---|---|---|
| 2,306,570 | A * | 12/1942 | Scripture, Jr. | 427/299 |
| 2,807,552 | A * | 9/1957 | Robinson et al. | 106/600 |
| 3,799,716 | A * | 3/1974 | Salts | 425/104 |
| 4,904,709 | A * | 2/1990 | Hermele | 523/220 |
| 5,110,364 | A * | 5/1992 | Mazur et al. | 134/2 |
| 6,218,012 | B1 | 4/2001 | Rota et al. | |

FOREIGN PATENT DOCUMENTS

| | | |
|---|---|---|
| WO | WO/98/29731 A1 | 7/1998 |
| WO | WO/01/60930 A2 | 8/2001 |

OTHER PUBLICATIONS

Hooker, Changing the face of Masonry, masonry Construction, Dec. 1991,pp. 470-472.*

"Exterior Wood Stains & Varnish with Resydrol," Coatings World, Mar. 1999, retrievied from the internet on Nov. 26, 2003 from www.coatingworld.com/march99form.htm.

Hooker, "Changing the face of masonry," Masonry Construction, Dec. 1991, pp. 470-472, retrieved from the internet on Nov. 25, 2003 from www.nawkaw.com.au/nawkaw-media-published.asp.

Formulary pages index by month, Coatings World, retrieved from the internet on Nov. 26, 2003 from www.coatingsworld.com/formarchive2.htm.

"About coatings world," Coatings World, retrieved from the internet on Nov. 26, 2003 from www.coatingsworld.com/about1.htm.

Brick Industry Association, "Technical Notes on Brick Construction," Dec. 2006, www.gobrick.com.

Materials & Engineering/Whitewares: Ceramic Engineering and Science Proceedings, Borate Fluxes in Ceramic Bodies, vol. 23, Issue 2, Abstract from Wiley InterScience, printed on Mar. 31, 2009.

Zemex Minerals Group, Inc., http://www.genchem/zemex/, printed on Mar. 31, 2009.

* cited by examiner

*Primary Examiner*—Frederick J Parker

(57) ABSTRACT

A method of coating a masonry product or structure, in which a single coating of a tinting composition is made on the exposed surface of the masonry product or structure that maintains its look, feel or texture, the masonry product or structure being chosen for suitability by passing one or both of the following tests: A) Wet Area Method: 2 milliliters of water discharged onto the masonry surface within one second at 20-25° C. Will wet out approximately 6 to 34 square centimeters (1 to 5 square inches) of the masonry surface in one minute, or B) Total Absorption Method: 2 milliliters of water discharged onto the masonry surface within one second at 20-25° C. is completely absorbed into the masonry surface within the period of 10 to 60 seconds. The preferred tinting compositions are aqueous latex emulsions.

14 Claims, No Drawings

COLOURING MASONRY SURFACES

FIELD OF THE INVENTION

The present invention relates to a method of coating a brick or masonry structure and a method of producing a brick or masonry structure whereby a brick or masonry staining composition is applied to a brick and masonry structures after construction so as to make the brick and or masonry structure appear to have the look, feel or texture of the masonry product as it was prior to being tinted.

BACKGROUND OF THE INVENTION

Brick tinting has been a specialised process for a specialised market Brick tinting is used to repair brick wall colours so that when a building extension is constructed the new bricks can be made to match the old bricks. Other applications include the repair of builder's errors where they organise the delivery of incorrectly coloured bricks and the error is only noticed after construction has begun.

The brick tinting process is a highly specialised, labour intensive process and is thus expensive, but is sometimes the only remedy available. This is particularly the case when old structures require extensions, but the clays from which the original bricks were made are no longer available. This matching of colour can be crucial to adding extensions to heritage and national trust structures.

The brick tinting process is applied by coating each brick individually as the base colour of the brick must be taken into account, and the colour of the tint adjusted so as to ensure that the final result will be the desired colour.

Rendering, bagging and painting of bricks has been known for a considerable time but in all cases the final result produces a structure or appearance whereby the brick appears to be coated and the natural texture of the brick or masonry is modified. In some markets this an undesirable effect.

The applicant does not concede that the prior art discussed in the specification forms part of the common general knowledge in the art at the priority date of this application.

SUMMARY OF THE INVENTION

Throughout the specification and claims the term "reactivity" is used as measure of the speed and or extent of a masonry surface to wet out by absorbing into the surface. This reactivity characteristic is a function of the surface's porosity, the depth of pores, the structure and interconnected volume of those pores and is an indication of capillary action or suction available to absorb a tinting composition. There are proposed two methods of testing reactivity of a masonry surface, the first test being the Wet Area test and the second being the Total Absorption test, both of which are hereinafter defined in the description below.

The present invention provides a method of producing a masonry structure, said method including the steps of:

selecting or producing a masonry product having one or more face surfaces with a reactivity equivalent to a wet out area of approx 1 to 5 square inches (6 to 34 square centimeters) by the Wet Area Method as herein defined or within approx 10 to 60 seconds by the Total Absorption Method as herein defined;

constructing a e with said masonry product so that said face surfaces form an exposed surface;

applying a tinting composition by a single application to the exposed surface of said masonry product, such that said tinting composition colours said exposed surface and maintains a look, feel or texture of the masonry product Preferably the Wet Area Method results in readings in the range of approx. 2 to 4 square inches (12 to 24 square centimeters).

Preferably the Total Absorption Method results in total absorption times of approx. 20 to 30 seconds The step of constructing said structure includes the laying of said masonry product in a stonework or brickwork fashion, with a mortar join between adjacent individual masonry products.

The mortar used can be of the same or similar reactivity to a face surface of said masonry product. The mortar can be struck so that it is finished flush with a face surface of said masonry product. The masonry product and the mortar can both be tinted with said composition.

Alternatively, the mortar can struck so that it is recessed relative to a face surface of said masonry product. By this means the masonry product only will coloured with said composition.

As an alternative, the mortar used can have a reactivity which will not absorb said tinting composition, when compared to the reactivity of said masonry product and will not absorb said composition. This mortar can be struck so that it is finished flush with the face surface of said masonry product The masonry product and said mortar can be both coloured with said composition, with said mortar being washed, by water gun or other means, to remove said composition which has not been absorbed.

The masonry product can be a clay brick which is produced by means of applying a slurry at least to those surface of said brick which will be exposed when in the structure to be built from said brick, said slurry being fired with said clay brick in a kiln. The slurry can be composed of water, fireclay, CALGON® or surfactant, glass cutlet or feldspar or borax. The slurry also include dried fine sand, or have dried fine sand applied thereto after the slurry has been added to the exposed faces of the brick.

The invention also provides a method of coating a masonry structure, said method including the steps of testing reactivity of a masonry product as used in said masonry structure; if the reactivity of the exposed surfaces of the masonry structure is the equivalent of a wet out area of 1 to 5 square inches (6 to 34 square centimeters) by the Wet Area Method as hereinbefore defined or within 10 to 60 seconds by the Total Absorption Method as hereinbefore defined; applying a tinting composition by a single application to the exposed surface of said masonry product, such that said tinting composition colours said exposed surface and maintains a look, feel or texture of the masonry product.

Preferably the Wet Area Method results in readings in the range of approx. 2 to 4 square inches (12 to 24 square centimeters).

Preferably the Total Absorption Method results in total absorption times of approx. 20 to 30 seconds In the method the masonry product and a mortar joint between adjacent masonry products can both be coloured with said composition. Alternatively, the masonry joint between adjacent masonry products can be insufficiently reactive so as to not absorb said composition, but has said composition applied thereto, with said mortar being washed to remove said composition which has not been absorbed.

The method can include the step of modifying the reactivity of the exposed surfaces of said masonry product as used in said structure, so that the modified reactivity thereof is as described above. This step of modifying the reactivity can include one or more of the following: pre-coating with a mineral paint based on a silicate chemistry of sodium or potassium; the use of absorbent sands in a concrete mix, and the use of light coloured cement, acid washing such as with muriatic acid, or immersions being applied to the cured structure prior to tinting in order to open up the pore structure to produce the defined reactivity.

The present invention also includes a masonry structure being produced or coated by the above described methods.

The present invention provides a masonry tinting composition having as its base an acrylic latex or alkyd emulsion prepared for translucent application of colour by means of colourants, said composition further including colourant added in the range of 2 to 20 US ounces of colourant per US gallon of emulsion. The colourant can be an oxide with colourant or an azo dye or colourants synthesised to an organic compound that imparts colour under visible light or daylight.

There can be included a water repellent, this water repellent can be such as that produced by Wacker Chemie and bears product code BS1306 or equivalent. The water repellent can be present in the range of 10 ml to 110 ml per US Gallon. The water repellent and emulsion can be homogenised by means of slowly adding the repellent to the emulsion, while the emulsion is being stirred which produces a mixing vortex in the emulsion. Other types of appropriate water repellent can also be utilised.

The composition can include a sun block compound. A sun block compound which can be used is that known by the trade mark TINUVIN as manufactured by Ciba Specialty Chemicals Inc, and more specifically the product which bears the code TINNUVIN 292 and or TINUVIN 1130. The sunblock compound can be present in the range of 0.1% to 8% by volume. Other types of appropriate sunblock agent can also be utilised in accordance with manufacturer's recommendations.

The composition can have a viscosity measured at 22 to 23 degrees Celsius by means of a Ford No 4 cup in the range of approximately 10 to 30 seconds, or of the same viscosity as measured by other means. More specifically the composition has a viscosity measured at 22 to 23 degrees Celsius by means of a Ford No 4 cup in the range of approximately 12 to 15 seconds, or of the same viscosity as measured by other means.

The composition can achieve the viscosity by means of dilution with water in the range of 30% to 45%. More specifically the composition can be diluted with water in the range of 35% to 40%.

A method of producing a masonry unit, said method including the steps of: selecting or producing a masonry product having one or more face surfaces with a reactivity equivalent to a wet out area of approx 1 to 5 square inches (6 to 34 square centimeters) by the Wet Area Method as hereinbefore defined or within approx 10 to 60 seconds by the Total Absorption Method as hereinbefore defined; applying a tinting composition by a single application to the exposed surface of said unit, such that said tinting composition colours said exposed surface and maintains a look, feel or texture of the masonry product.

When the masonry unit is a clay brick it can be produced by means of applying a slurry at least to those surfaces of said brick which will be exposed when in the structure to be built from said brick, said slurry being fired with said clay brick in a kiln, if the clay from which the brick is does not, after firing produce a face surface with the required reactivity. The slurry can be composed of water; fireclay, CALGON® or surfactant, glass cutlet or other fluxes, or clay suspension sources such as shales. The slurry can also include dried fine sand.

Alternatively the masonry unit can have the requisite reactivity after firing or setting without application of a slurry or pre-treatment.

Further the masonry unit can pretreated by means of one or more of the following:

pre-coating with a mineral paint; the use of absorbent sands in a concrete mix; the use of light cement or acid etching or washing of the surface.

Multiple ones of said masonry units, or batches of said masonry units can have said tinting composition applied to exposed faces thereof in a single application pass.

Through out this specification and claims the word "masonry" will be understood to include brick, concrete, stone, fibre reinforced cement sheeting and other masonry, unless otherwise specified.

DETAILED DESCRIPTION OF THE EMBODIMENTS AND EXAMPLES

Example 1

Tinting Composition

The tinting composition is made from a base which is an acrylic latex or alkyd emulsion, such as that prepared for translucent application of colour via oxides or colourants to substrates such as wood, concrete, stone etc. Such a base can include the following constituents:

| Constituents | Estimated Percent by weight |
|---|---|
| Acrylic Resin | 26.3 |
| Nuosept 95 | 0.3 |
| Nuocide 404-D | 0.7 |
| Nepheline syenite | 6.0 |
| Ethylene Glycol | 2.0 |
| Cellulosic Thickener | 1.5 |
| Water | 63.2 |

The NUOCIDE 404-D & NUOSEPT 95 are proprietary preservatives made by International Specialty Products Inc, and can be replaced by other similar products.

Nepheline syenite is a "Flatting Pigment" and is available under the trade mark MINEX as manufactured by Unimin Specialty Minerals. The nepheline syenite can be replaced by similar anti-gloss or flatting pigment compounds.

Ethylene Glycol is present as a coalescing solvent and freeze-thaw agent It can be replaced by similar products such as TEXANOL produced by ICI.

Suitable characteristics for the base polymer emulsion for use in this example, would be those typical of base polymer emulsion of a premium wood stain:

| Characteristic | Quantity |
|---|---|
| SG | 1.2-1.35 |
| Viscosity 72 F. | 70-95 KU |
| % solids(wt) | 35-40% |
| % solids(vol) | 30-35% |
| pH | 8.0-9.5 |
| Gloss | Flat |
| Flash Point | None |
| Volatile organic compounds %. | <5% |

To this base 10 US oz per US gallon of oxide suspension with colourant is added. If desired as an alternative, 10 US oz per gallon of organic colourant suspension or paste colourant could be added.

This composition is then shipped to the building site and then diluted by 35% to 40% of water.

With such a composition the colour formulation does not need adjusting on site and to a limited extent, the colour formulation does not rely on the substrate colour of the brick for its final colour.

Once applied to a masonry surface having the required reactivity, it is expected, depending upon ambient conditions at the time of application, that it will take of the order of 5 to 30 minutes for the tinting composition to be de-watered and cross-linking commencing whereby acrylic latex bonding will have commenced.

Example 2

Water Repellent Tinting Composition

To the base of Example 1 is added 70 milliliters per US gallon or an estimated 0.4% percent by weight of the composition of Wacker Chemie BS1306 water repellent which is mixed through the emulsion. The water repellent and emulsion are homogenised by means of stiring the emulsion with an impeller on a rotating shaft so as to cause a mixing vortex to be present in the emulsion, with the water repellent being trickle fed into the vortex to produce an homogenised product. This slow yet vigorous mixing will counter any unfavourable volume ratios and or viscosity gradients which might normally be encountered in such dilutions.

To this base 10 US oz per US gallon of oxide suspension with colourant is added. If desired as an alternative, 10 US oz per gallon of organic colourant suspension or paste colourant could be added.

This composition is then shipped to the building site and then diluted by 35% to 40% of water.

With such a composition the colour formulation does not need adjusting on site and to a limited extent, the colour formulation does not rely on the substrate colour of the brick for its final colour.

The water repellent is an option in the tinting composition and is added only so that the freestanding masonry or masonry exposed to the weather, after it has been treated with tinting composition, readily sheds water and is easier to clean and remains clean in service. The Wacker Chemie BS1306 is the preferred water repellent, but any appropriate water repellent can be utilised, in accordance with manufacturer's recommendations.

Example 3

Tinting Composition With Sunblock Additive

To the composition of examples 1 and or 2, sun-blocking or UV absorbent compounds can be added to give the applied composition sunblock capability to prevent fading and increase life.

A suitable sunblock or UV absorbing additive is sold under the trade mark TINUVIN by Ciba Specialty Chemical Inc . In particular Tinuvin 292 and Tinuvin 1130 are preferred. The amount utilised will be dependent upon the type and duration of protection desired. The manufacturer's recommendations can be followed. In the case Tinuvin 292 and Tinuvin 1130 is the total amount used can be between 2% and 8% by weight of the composition.

When adding UV absorbent additives which tend to have relatively high viscosities, it is important to ensure thorough mixing occurs in order to remove any viscosity gradients which may otherwise result.

Example 4

Another Latex Emulsion Tinting Composition

Another latex emulsion base, that is expected to give a similar result to that described in examples 1 to 3 above, has the following composition:

| Constituents | Estimated Percent by weight |
|---|---|
| Resydrol AY586 w/45% in water | 44.57 |
| Mineral Spirits | 3.87 |
| Acrosolv DPM | 3.06 |
| Additol VXW 6206 | 0.41 |
| Additol XL250 | 1.20 |
| Troykya Anti skin B | 0.26 |
| BYK 035 (Byk Chemie) | 0.07 |
| BYK 341 | 0.30 |
| Troysan Polyphase P20 T | 0.85 |
| Acrysol RM 8W | 0.04 |
| Acematt TS 100 Degussa | 0.83 |
| Water | 44.54 |

The Viscosity of this base is approx 20 seconds on Ford No 4 cup To this base 10 US oz per US gallon of oxide suspension with colourant is added. If desired as an alternative, 10 US oz per gallon of organic colourant suspension or paste colourant could be added.

This base does not include any UV absorbers and these can be added.

Measured Viscosity Data of the Tinting Composition

The viscosity of the tinting composition is an important factor for the ability to apply the tinting composition in a single application, to achieve the desired colour density.

The data which follows are viscosity measurements of the tinting composition of Example 3, (Example 1 and 2 would achieve much the same results) using a Ford No 4 cup at 22° C. to 23° C., starting with one liter and adding $H_2O$ by volume and recording the time for the cup to empty:

| Concentration | Time to empty (seconds) |
|---|---|
| Undiluted | 27.7 |
| Diluted by 100 ml water added | 20.3 |
| Diluted by 200 ml water added | 16.6 |
| Diluted by 300 ml water added | 15.0 |
| Diluted by 400 ml water added | 12.3 |
| Diluted by 500 ml water added | 12.1 |
| Diluted by 600 ml water added | 11.7 |
| Diluted by 700 ml water added | 11.4 |
| Diluted by 1000 ml water added | 11.1 |
| pure water | 09.5 |

As a comparison, paint was also tested and resulted in times of the order of four minutes to drain through the cup.

The viscosity range required for the tinting composition of the examples above are achieved by means of a 35%-40% dilution with water and will result in a Ford cup No 4 reading of approximately 12-15 seconds.

A reading of 50 seconds or greater would render the tinting composition incapable of penetrating the masonry surface and would thus give a painted or non-authentic look.

A reading of 40 seconds would lead to overlap marks during application and thus also not result in a suitable finish.

While the preferred reading is 12 to 15 seconds, a reading in the range of 10 to 30 seconds is thought to be able to produce desirable results.

The Masonry Surface to be Tinted

The reactivity of a masonry surface ("reactivity" being a characteristic of a surface which is a function of the porosity, the depth of pores, the structure and interconnected volume of those pores) is an indication of the capillary action available to absorb the tinting composition. This capillary action, if finite and restricted, will determine whether the tinting composition can be applied as a single coat, and whether the tinting composition will remain in the masonry surface for a sufficient length of time. As to what may be a sufficient length of time will be discussed below.

The masonry surface to be tinted is best if it is of a light colour and has a pore depth, structure and interconnected volume that will accommodate one application of the tinting composition. The appropriate colour and reactivity will ensure that a masonry surface will react to the tinting composition in an even manner (not varying in colour depth and thus not patchy in appearance). The tinted surface will appear as authentic as the original surface but will simply have changed colour evenly, as the bulk, if not all, of the tinting composition will reside either within the masonry surface and/or below the masonry surface.

The masonry surface to be tinted can includes bricks, blocks or stones as well as the mortar joint if desired, all of which can be coloured by the tinting composition.

The WET AREA METHOD—A Measure of the Reactivity of a Masonry Surface.

While several tests could be used to identify the level of reactivity of a masonry surface, the following Wet Area Method has been found to be a most useful one:

Step 1: Orient a dry brick into a horizontal position with its face surface to be tested facing up at a location being at a room temperature of between 20° C. and 25° C.

Step 2: Load 2 milliliters of water into a lab syringe, pipette or other liquid measuring device.

Step 3: Discharge the 2 milliliters of water onto the centre of the brick face surface within one second.

Step 4: Measure and observe wetting out/absorption behaviour of the brick surface for one minute from discharge of water onto brick face.

A non reactive surface, that is one which will not be suitable for use with the tinting composition in that it would not be satisfactorily recoloured in a one stage absorption process, will have water beading and sitting on top of the brick surface, with only a relatively small portion having been absorbed within one minute.

A suitably reactive brick surface, which would be suitable for use with the tinting composition and which will absorb sufficient composition in a single application, will show a markedly different absorption behaviour.

Preferably a suitable reactive surface will have the 2 milliliters of water rapidly wetting out the brick surface and spreading to an area of 1 to 5 square inches (6 to 32 square centimeters) or more preferably of 2 to 4 square inches (12 to 25 square centimeters) visibly wetting the brick face.

The TOTAL ABSORPTION METHOD—Another Measure of the Reactivity of a Masonry Surface.

A second test of the reactivity of a surface is called the Total Absorption Method and utilises steps 1 to 4 of the previous test, however, this test requires a recording or noting of the time taken to have the 2 milliliters of water completely absorbed by the masonry surface.

For the purposes of this invention, a suitable reactivity is present if within 10 to 60 seconds and more preferably 20-30 seconds from the application of the 2 milliliters of water, all of the water on the surface will have been absorbed into the masonry surface with none visibly remaining on the surface.

The Total Absorption Method and the Wet Area Method can be determined from one procedure and do not have to be separately conducted.

Bricks and Slurry Compositions

Producing an appropriately reactive surface on a kiln fired clay bricks can be done by applying a tailored fireclay/ballclay kiln fired slurry coating to external brick faces.

A full and even coverage of slurry is applied to the external faces of the brick. Sand can be incorporated in the slurry to bulk the slurry and aid as a parting sand during manufacture of the brick. This sand also adds to the reactivity of the slurry surface as does sawdust and similar materials, that creates extra pore volume and area by inclusion in the slurry composition.

The slurry surface can be adjusted, by means of changing the proportions of the contents of the slurry to accommodate more or less of the tinting composition as is necessary for different effects. Further, sand or other stable fillers can be added to the slurry mixture so as to create different surface effects after the tinting composition has been applied.

Essentially and generally speaking, the slurry is an aqueous suspension of fireclay and water with a flux added (usually in the form of cullet and or feldspar). In addition a dried sand is incorporated into this slurry. This sand is added to aid in parting in the production of a conventional brick. The aqueous suspension is facilitated by the addition of the dispersing agent or suspension into the slurry.

To achieve the desired results, the depth, reactivity and porosity of the slurry is enhanced by deliberately adding more sand or increasing the rate of application of the slurry and applying a sprayed application of fine dried sand. The sand is incorporated in the slurry as it de-waters on the brick column during the extrusion process.

The ingredients of the slurry can include: fireclay, CALGON® or surfactant (to aid suspension of fireclay particles); glass cullett or mineral feldspar (to lower the temperature of formation of ceramic bond of slurry to brick); water; dried fine sand.

No colorants or oxides are added to the slurry as the tinting composition provides the colour.

The cullett level is reduced from standard levels to minimum requirements whilst still manufacturing a clay brick with a sound and durable fired slurry bonded to the brick to prevent the slurry from glassing up, which would otherwise decrease the reactivity of the resulting surface.

The slurry can be applied by any appropriate means, such as spraying from stationary or moving nozzles, application by brush, flooding by hose and spreading by roller or other appropriate method, over a moving brick extrusion column. Other bricks can also be used with suitably reactive coatings being applied such as bonded ceramic sand coatings ( which are a variation on a slurry or engobe) in soft mud moulded brick manufacture.

The following are specific examples of suitable slurries:

| White coloured slurry formulation | |
|---|---|
| Component | Quantity |
| Kaolin clay (white clay high melting temp.) | 125 kg |
| Glass Cullet (broken glass ground (flux agent) | 100 kg |
| CALGON ® (Dispersant) | 2 liters |
| Water | approx 130 liters. |

The water in the above composition is varied to achieve a desired viscosity of the agitated homogeneous suspension. The viscosity of the slurry should fall in a range of 18-22 seconds Ford Cup No. 4. The quantities are increased for the above slurry composition at the same ratios for bigger manufacturing runs.

In the formulation above there is no colorant added as the white is derived from the Kaolin clay, which can be purchased in bagged form.

The amount of flux is varied depending on the firing behaviour of the base clay mix in the brick and also kiln and kiln equipment limitations.

Instead of using kaolin other clays that form the suspension can be employed depending on availability and commercial factors. These include but not are limited to: ball clay, fire clay; milled shales (ball clays); mined clays; bagged ball clays; shales; kaolin. These dry fine clays are able to be incorporated in suspension. The choice might depend on the colour required but depend on the fired colour of the ball clay or milled shale (or shale blends).

The water is added to the suspension to vary the viscosity to the target value for de-watering and spreading purposes.

The dispersing agents used are surfactants that promote suspensions. These include but are not limited to: CALGON®; DISPEX®.

The colourants are added for effect and are usually inorganic glass body stains. These also include but are not limited to: ground colour imparting clays and shales; manganese dioxide or manganous oxide; Tiona Ferro Corporation markets and sells most additives for coloured slurries.

The fluxing agents are used to bond the coating and a combination of: the type; addition levels; and the firing temperature that is employed to bond the slurry to the brick, govern the physical absorbency and also partly the reactivity to post colouration. These fluxes include but are not limited to: glass cullet (ground); mineral feldspar powder; shales/clays containing enough natural fluxes; potassium and sodium carbonates. Generally it will be economic considerations that determine which flux is used.

| Grey coloured slurry formulation. | |
|---|---|
| Component | Quantity |
| Local light coloured shale | 1375 kg |
| Manganese Dioxide | 18 kg |
| DISPEX ® | 2 liters |
| Water | Approx 1000 liters. |

The target viscosity for this grey coloured slurry formulation is 13 secs for Ford No 4 cup test.

Another slurry formulation includes:

| Light coloured slurry formulation | |
|---|---|
| Component | Quantity |
| Ball Clay R | 1300 kg |
| Ceramic Glaze Frit | 235 kg |
| Tiona | 35 kg |
| DISPEX ® | 1.7 liters |
| Water | Approx 1200 liters. |

The target viscosity for this grey coloured slurry formulation is 20 secs for Ford No 4 cup test.

A further slurry formulation is:

| Slurry formulation to receive tinting composition | |
|---|---|
| Component | Quantity |
| Kaolin | 1300 kg |
| CALGON ® | 2.2 liters |
| Mineral Feldspar | 150 kg |
| Water | Approx 1200 liters |
| Fine white washed sand | added to excess after slurry dosing. |

The target viscosity for this preferred slurry formulation is 21 sees for Ford No 4 cup test.

This preferred reactive slurry is similar to those previously described but has been modified to be slightly more viscous and full in its coverage. When it is applied it has a feed rate which is increased so that it is essentially flooding the extrusion column surface. The excess slurry is mopped up evenly by a spray application of the fine dry white washed sand.

The preferred slurry also differs in that the flux agent addition levels have been lowered so as to aid the absorption of the tinting compositions described above and to also even out and minimise fired colour variations resulting from natural temperature differentials. There are no colorants added as none are necessary.

The flux selection and addition levels of the preferred slurry formulations, as with previous formulations, are tailored to the clay body of the brick and the firing regime within the kiln.

Concrete Based Masonry

For suitable concrete block, concrete roof tile and other masonry surfaces, the tinting composition can be applied with useful results if the masonry surface has been modified via an appropriate treatment that results in a level of reactivity which is discussed above.

An appropriate pre-treatment can include precoating with a mineral paint, the use of absorbent sands in the concrete mix, applying an acid etching or washing to open the pores such as with muriatic acid, or immersions being applied to the cured structure, and the use of light coloured cements. These pretreatments modify the masonry surface so as to receive the tinting composition as the pore structures will have been opened and the pore depths win have been limited to create the right site for a one stage colour absorption.

Mortar Joints

Mortar joints that are to be recoloured by the tinting composition need to be specific with regards to their mortar composition. The best mortar joints are essentially a combination of off white or bright Portland cement and a suitable light coloured sand (a light coloured sand is one that contains not too much clay or too little clay whether this clay content occurs naturally or it is added as required).

Where a "sharp" sand is to be used with a light Portland cement, it should be modified to make the mortar mix more workable and in doing so the dried mortar joint will be sufficiently reactive so as to take the colouring process in a one stage roller application. The sharp sand can be modified by adding either lime to the mix at approx 5-10% addition levels or by adding approx 5%-10% of fireclay (also known as "Brickie's clay"). Alternatively the ratio of cement to sand can be increased for example from 6:1 to 4:1 by volume with little or no addition of clay or hydrated lime.

The precise amount of fireclay required is determined by first conducting a wet sieve test washing the sand through a 45 micron sieve and determining the weight loss on an oven dried basis. The weight loss win be approximately the natural clay and silt content of the sand. Any shortfalls in the natural clay are topped up by the appropriate addition of fireclay.

Mortar Finish Details to Receive the Tinting Composition

To properly apply the tinting composition to a mortar joint it should be cut flush and full with the brick/block edge for a monolithic uniform look where the mortar colour matches the brick/block colour.

If a non-monolithic look or traditional brickwork appearance with defined and contrasting mortar joints is required, then it will be best if the joint is raked or recessed so that the mortar does not come in contact with the tinting composition during the application process.

If desired, a non reactive mortar can be used and cut flush with the brick/block. Such a non reactive mortar may be produced by the addition of a bonding agent or sealer. In this case, by applying the tinting composition all over the brick/block and the mortar, the tinting composition will not adhere to the mortar and can be washed away by any appropriate means including by water gun or jet.

Application of the Tinting Composition

If the tinting composition is prepared as described above and applied by a roller having a 12 mm to 20 mm nap (with a 12 mm nap being preferred) then the tinting composition of examples 1 to 3 does not overlap during absorption because it is drawn below the masonry surface.

The nap measurement of a roller is the pile length of the roller material.

While a roller is the most preferred application method, other methods, such as spraying or brushing or other means can be utilised so as to achieve, by a single application of a tinting composition, onto a masonry surface having the reactivity as herein defined, so that once tinted the masonry surface will have the look and or feel and or texture of a masonry surface. It is also believed that the masonry surface will maintain its ability to breathe, maybe not to the same degree as prior to tinting, because the tinting composition will enter into the pores of the masonry surface and coat them but not seal them.

Production of Colour

The tinting composition is such that the final applied colour of the tinted masonry, is essentially designed from the colourants alone. While a light or white background of the masonry surface being tinted is helpful, the background colour need not be a factor.

Duration or Life of the Tinting Composition

The level of sunblock compound added to the tinting composition will, together with the reactivity of the masonry surface, determine the life of the tinting composition as applied to the masonry surface. While for some applications a life of 25 years is desirable, in other applications a life of 5 to 10 years will be desirable. For example, a home owner may decide, at the time of building, that they will want to be able to change the colour of the bricks and or mortar, say at 10 year intervals, and yet retain the look, feel, texture, appearance of a brick work surface. In this circumstance, the level of sunblock compounds added can be varied to achieve a desired life of the tinting composition.

In addition, the use of water repellents and UV absorbers or sun block compounds for interior applications on brickwork and masonry might be dispensed with altogether.

Production of a Masonry Unit

A masonry unit, such a s brick or block, whether of fired clay or stone can be manufactured and delivered to a building site pre tinted by a tinting composition.

Such a masonry unit can be manufactured whereby the unit is selected or produced with one or more face surfaces having a reactivity equivalent to a wet out area of approx 1 to 5 square inches (6 to 34 square centimeters) by the Wet Area Method as hereinbefore defined or within approx 10 to 60 seconds by the Total Absorption Method as hereinbefore defined.

Once the desired reactivity is present, a tinting composition can be applied by a single application to the exposed surface of said unit, such that said tinting composition colours said exposed surface and maintains a look, feel or texture of the masonry product.

When the masonry unit is a clay brick, if the clay brick when fired would not have the required reactivity, then before firing, it can have a slurry, such as one described above, applied to the brick to at least to those surfaces of said brick which will be exposed when in the structure to be built from the brick. Then the slurry can be fired with the clay brick in a kiln.

Otherwise the masonry unit can have the requisite reactivity after firing or setting without application of a slurry or pretreatment.

If the masonry unit does not have the required reactivity, then it can be pre-treated by means of one or more of the following: pre-coating with a mineral paint; the use of absorbent sands in a, concrete mix; the use of light cement or acid etching or washing of the surface.

To maintain a good rate of production the tinting composition can be applied by means of a spraying system.

By this means the cost of production of the brick is expected to be reduced by reducing the complexity and reducing the costs of materials to produce a variety of colour ranges.

A masonry unit produced by this method can then be used in construction in the same way as any other brick or block.

It will be understood that the invention disclosed and defined herein extends to all alternative combinations of two or more of the individual features mentioned or evident from the text. All of these different combinations constitute various alternative aspects of the invention.

The foregoing describes embodiments of the present invention and modifications, obvious to those skilled in the art can be made thereto, without departing from the scope of the present invention.

The invention claimed is:

1. A method of tinting a masonry surface, comprising:

applying a slurry to a masonry surface comprising a clay brick to form a slurry-coated clay brick, wherein said slurry comprising an aqueous suspension of water, clay, sand, flux, and no added colorants or oxides;

firing said slurry-coated clay brick, thereby bonding said slurry to said clay brick to form a masonry product, wherein a flux level is selected to prevent the slurry from glassing when the slurry-coated clay brick is fired; and applying a tinting composition to said masonry product, such that said tinting composition colours said masonry product.

2. A method according to claim 1, wherein said clay comprises kaolin or a ball clay.

3. A method according to claim 1, wherein said flux is selected from the group consisting of glass cullet, feldspar powder, fire clay, potassium carbonates, and sodium carbonates.

4. A method according to claim 1, wherein said flux comprises glass cullet or potassium carbonates.

5. A method according to claim 1, wherein adding sand to the slurry increases pore volume of an external surface of the clay brick.

6. A method according to claim 1, comprising adding sand to the slurry after the slurry is applied to an exposed surface of the clay brick.

7. A method according to claim 6, wherein said adding comprises spraying an application of dried sand.

8. A method according to claim 1, comprising incorporating sand into the slurry as it de-waters on a brick column during an extrusion process.

9. A method according to claim 1, wherein said slurry further comprises a surfactant.

10. A method according to claim 1, comprising applying a full and even coverage of slurry to external surfaces of said clay brick.

11. A method according to claim 1, wherein said tinting composition comprises an acrylic latex or alkyd emulsion base.

12. A method of tinting a masonry surface, comprising:

applying a slurry to a masonry surface comprising a clay brick to form a slurry-coated clay brick, wherein said slurry comprising an aqueous suspension of water, clay, flux, and no added colorants or oxides;

spraying sand into the slurry as the slurry de-waters on the clay brick;

firing said slurry-coated clay brick, thereby bonding said slurry to said clay brick to form a masonry product; and applying a tinting composition to said masonry product, such that said tinting composition colours said masonry product.

13. A method according to claim 12, wherein said tinting composition comprises an acrylic latex or alkyd emulsion base.

14. A method of producing a reactive surface on a clay brick, comprising:

applying a slurry to a masonry surface comprising a clay brick to form a slurry-coated clay brick, wherein said slurry comprising an aqueous suspension of water, clay, sand, flux, and no added colorants or oxides; and firing said slurry-coated clay brick, thereby bonding said slurry to said clay brick, wherein a flux level is selected to prevent the slurry from glassing when the slurry-coated clay brick is fired.

* * * * *